United States Patent [19]

Grim et al.

[11] Patent Number: 5,713,837
[45] Date of Patent: Feb. 3, 1998

[54] UNITARY ORTHOPAEDIC BRACE

[75] Inventors: Tracy E. Grim, Broken Arrow, Okla.; Joseph M. Iglesias, Agoura, Calif.

[73] Assignee: Royce Medical Company, Camarillo, Calif.

[21] Appl. No.: 580,129

[22] Filed: Dec. 28, 1995

[51] Int. Cl.$^6$ .................................................. A61F 5/00
[52] U.S. Cl. ........................... 602/6; 602/5; 602/21; 602/27; 602/22
[58] Field of Search ..................... 602/5-6, 20-23, 602/27; 128/DIG. 23

[56] References Cited

U.S. PATENT DOCUMENTS

| | | | |
|---|---|---|---|
| 667,768 | 2/1901 | De Puy | 602/6 |
| 4,382,439 | 5/1983 | Shen | |
| 4,520,806 | 6/1985 | Miller | 602/6 |
| 4,765,319 | 8/1988 | Finnieston et al. | |
| 4,768,502 | 9/1988 | Lee | 602/6 |
| 4,873,968 | 10/1989 | Finnieston et al. | |
| 4,928,678 | 5/1990 | Grim | |
| 5,134,992 | 8/1992 | Campbell, II | 602/23 X |
| 5,205,812 | 4/1993 | Wasserman | |
| 5,279,545 | 1/1994 | Reese, Sr. | 602/21 |
| 5,307,521 | 5/1994 | Davis | 602/5 X |
| 5,415,623 | 5/1995 | Cherubini | 602/6 X |
| 5,441,015 | 8/1995 | Farley | 602/27 X |
| 5,507,720 | 4/1996 | Lampropoulos | 602/23 X |

FOREIGN PATENT DOCUMENTS 9427529  12/1994  European Pat. Off. .............. 602/23

*Primary Examiner*—Linda C. Dvorak
*Attorney, Agent, or Firm*—Oppenheimer Poms Smith

[57] ABSTRACT

An orthopaedic brace for supporting a selected portion of the anatomy including a unitarily molded support having substantially flexible areas, substantially rigid portions for providing splinting action and a support coupling unitarily molded with the support for holding the opposed edges toward one another and for adjustably and removably securing the support onto the selected portion of the anatomy.

26 Claims, 7 Drawing Sheets

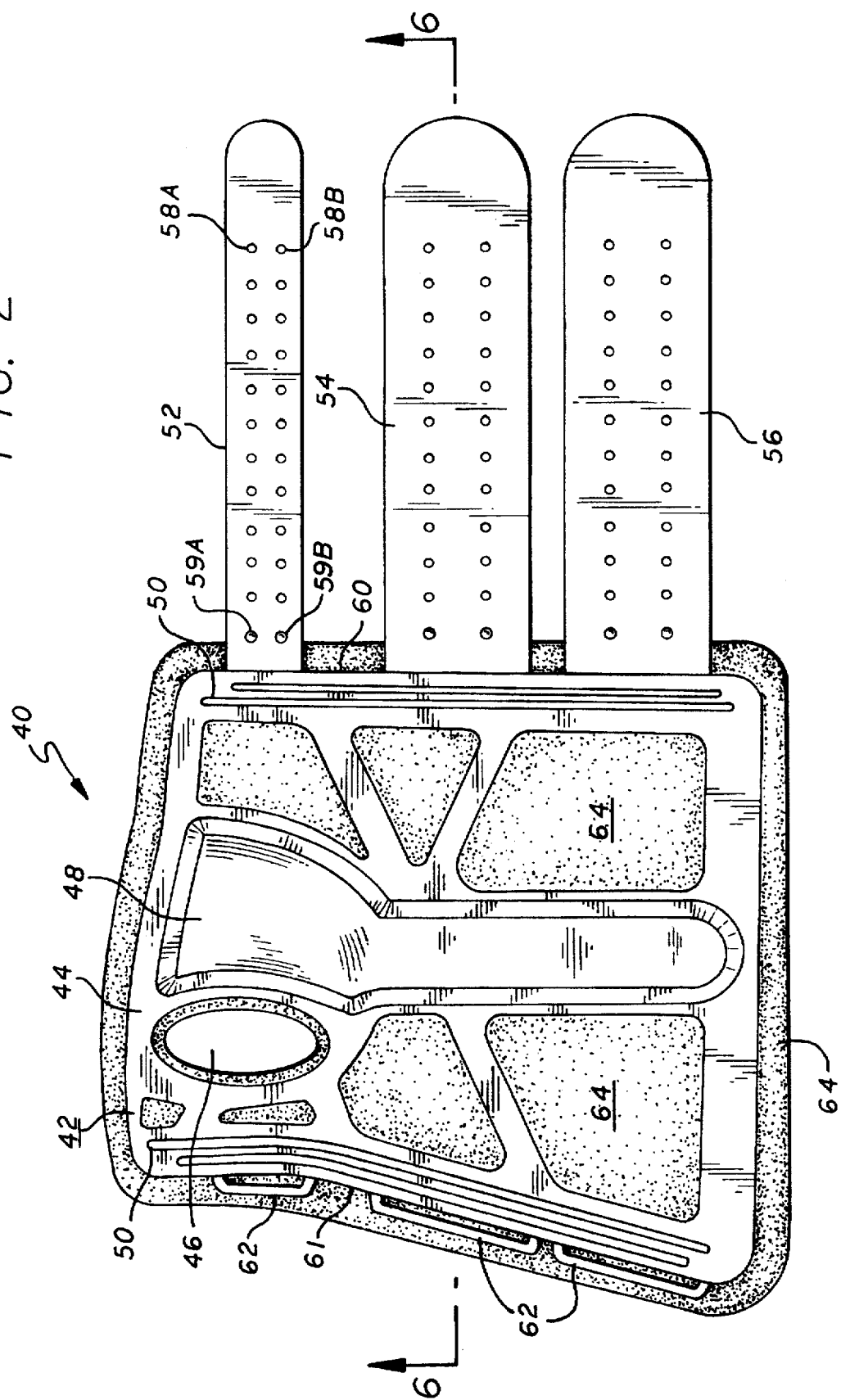

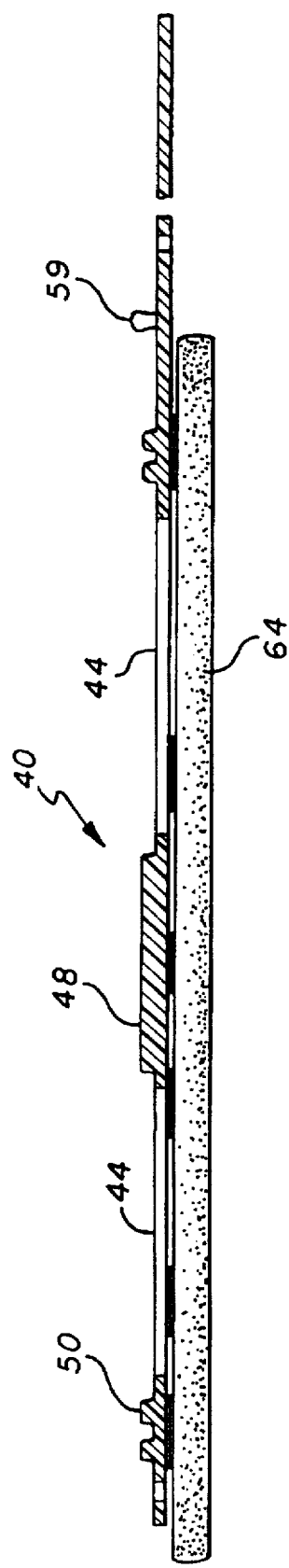
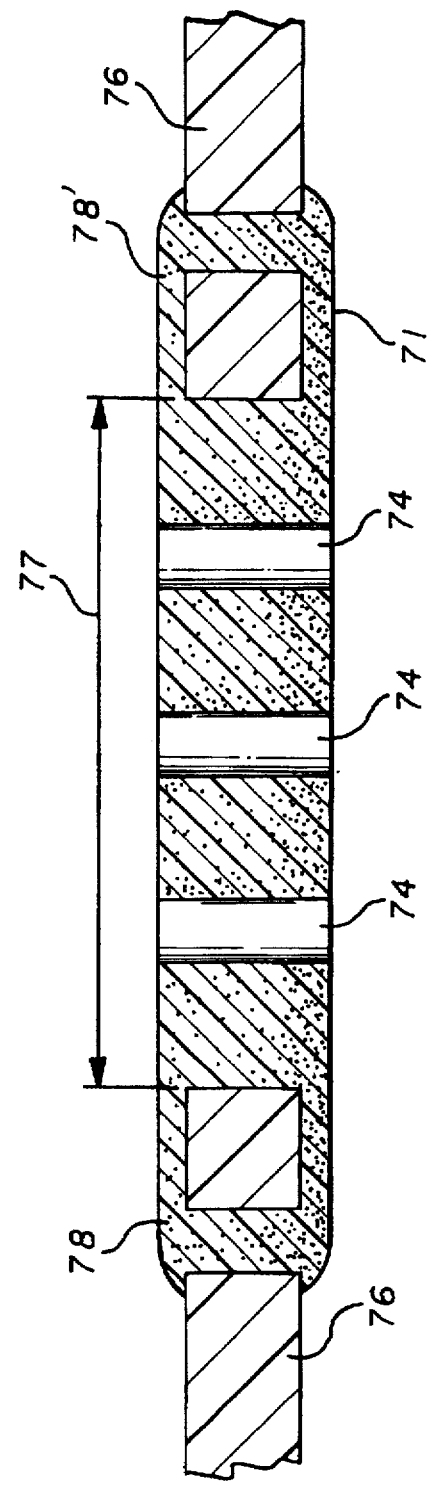

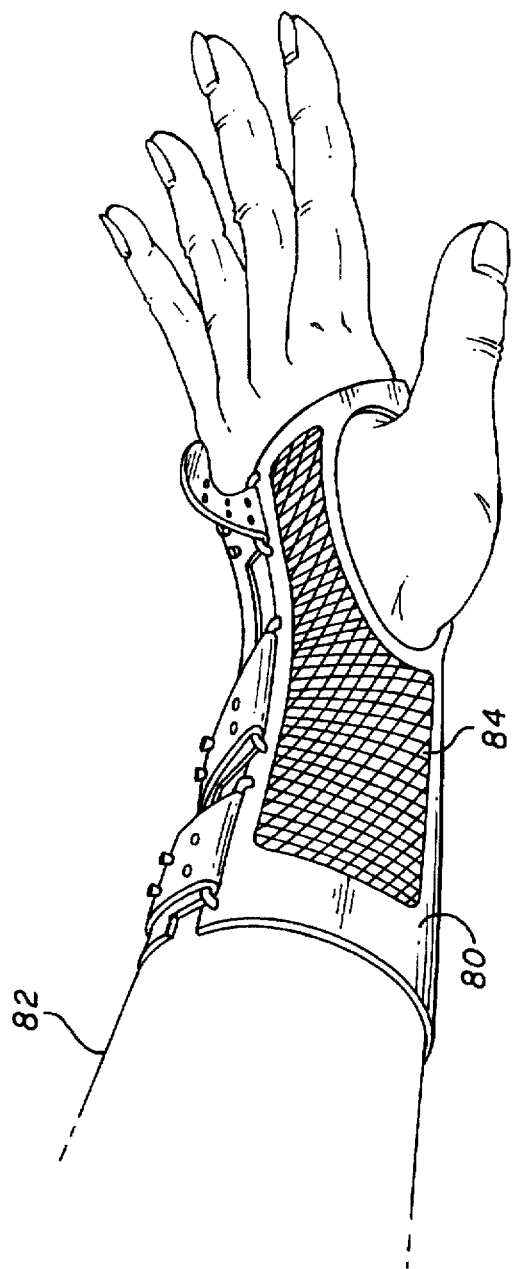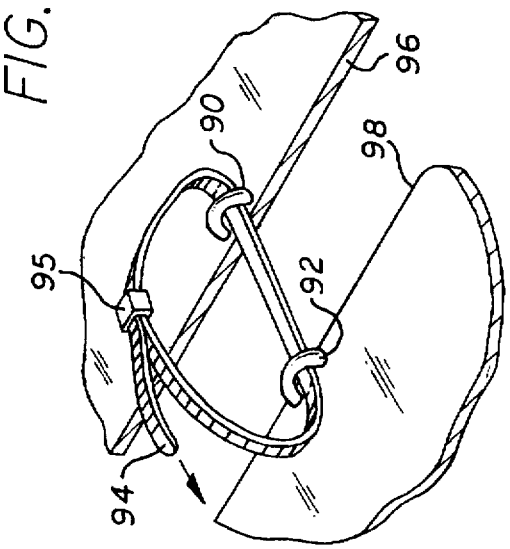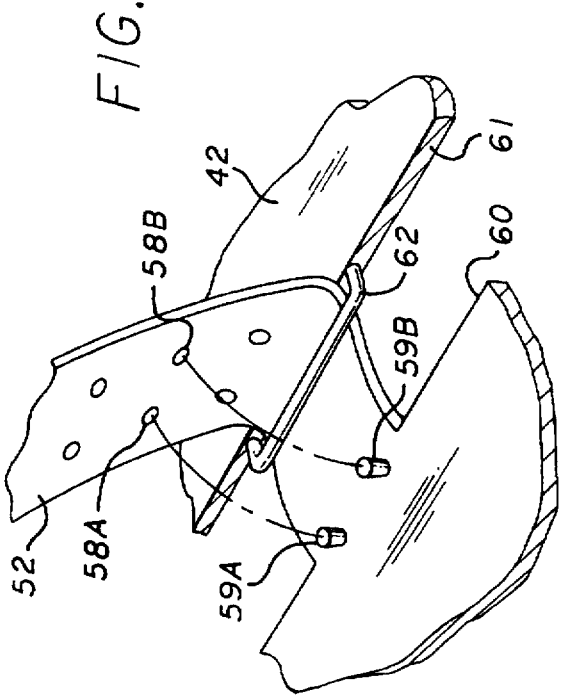

UNITARY ORTHOPAEDIC BRACE

BACKGROUND OF THE INVENTION

1. Field of the Invention

The present invention relates generally to orthopaedic devices and more particularly to orthopaedic braces or supports.

2. Description of the Related Art

Orthopaedic devices such as braces, supports and splints have long been available for supporting and immobilizing various injured or strained parts of the anatomy such as the wrist or the ankle. These orthopaedic devices provide protection and comfort to the patient and aid in the healing of those parts. Traditionally, softgood braces have been made using a method known as "cut and sew." This process involves carefully cutting numerous pieces of material from a pattern, arranging these pieces and sewing them together so that the resultant product takes on the general shape of a desired portion of the anatomy. Generally, a preshaped splint or stay constructed of stiff or rigid material, such as aluminum or plastic, is inserted and sewn into the brace to provide stability to or immobilization of the injured or strained portion of the anatomy, such as the wrist or ankle. The brace or support is often somewhat flexible and extends around the injured part of the anatomy, with the edges of the brace held together to securely fasten the brace to the body part. Straps are often attached to one edge of the brace to adjustably secure the two edges together. Commonly, hook and loop arrangements, also known as Velcro, are employed to hold the ends of the straps in their secured positions. Examples of braces or splints that employ the "cut and sew" manufacturing method, as well as Velcro-type strap arrangements, are disclosed in U.S. Pat. Nos. 4,382,439, 4,765,319, 4,873, 968, 4,928,678, and 5,205,812.

While the braces and supports shown in the above-mentioned references are adequate for some purposes, all suffer from a number of common drawbacks. Manufacturing these devices entails, first, the production or purchase of many discrete components and, second, the labor and time intensive, step by step, assembly of these components. Further, the sum of the costs of the components is significant. Finally, as the number of components and steps in a manufacturing process increases, the risk of human and machine error also increases, resulting in a greater amount of wasteful scrap. These factors translate into relatively high production costs and, consequently, expensive end products for patients.

Various attempts at reducing the labor intensiveness and high cost of manufacturing orthopaedic devices have been pursued. However, these devices have achieved only limited success. For instance, U.S. Pat. No. 5,368,549, issued to McVicker, discloses a product and method for unitarily molding Velcro-type hooks onto a relatively rigid portion of an orthopaedic device for mating to the loop portion of a separately attached strap. This product, however, merely eliminates one step in the manufacturing process: the requirement of attaching the hook portion of the fastener to the device. It does not eliminate the labor intensive steps of securing the loop material onto the straps and stitching, bonding or otherwise attaching the loop-carrying strap to the device and generally forming a complete orthopaedic brace or support.

SUMMARY OF THE INVENTION

The general purpose of the present invention is to provide an orthopaedic device which obviates, for practical purposes, the above-mentioned problems in the art. In particular, one object of the present invention is to provide an orthopaedic brace for use on a selected portion of the anatomy such that, in one manufacturing step, all, or substantially all, of the required components are unitarily molded. Another object of the present invention is to provide fully effective orthopaedic braces for use on selected portions of the anatomy that are low in cost.

A further object of the present invention is to provide a unitarily molded wrist brace that is formed in one step.

In order to accomplish these and other objectives, one preferred embodiment of the present invention involves a molded orthopaedic support having relatively thick areas for providing rigid splinting action, thinner flexible areas for conforming to and at least partially enclosing the part of the anatomy to be supported, and straps for securing the brace or support to the part of the anatomy to be supported.

Another preferred embodiment includes a unitarily molded wrist brace with open spaces in the thinner flexible areas for breathability, thicker areas to provide splinting action, support mounting arrangements and padding material mounted within the support to provide cushioning where the support engages the arm, wrist and hand.

Other features of the invention which may be employed include the following: post and hole arrangements on the securing straps for adjustably securing the support, D-rings integrally molded at one edge of the support for use with the straps, unitarily molded mesh zones for the thinly molded areas, and co-molding resilient material onto the support.

The present invention provides a number of advantages over the prior art. For example, the present invention does not require multiple steps in its construction. Injecting a single molding shot of any number of materials, such as polypropylene, polyethylene, thermoplastics, elastomers, nylon, or urethanes, into a preformed mold may create the final product or one which requires very little further processing. Therefore, extensive assembly labor and risk of manufacturing errors and flaws are virtually eliminated. Also, with appropriate configuration of the mold, areas of varying thicknesses can be created. Thicker and, therefore, stiffer areas can be molded at locations that require splinting action, while thinner, more flexible areas may make up the remaining portions. Furthermore, with advances in molding materials, the cost, comfort and, durability of the end product is greatly improved.

The foregoing and other features and attendant advantages of the present invention will become apparent from a consideration of the following detailed description when considered in conjunction with the accompanying drawings.

BRIEF DESCRIPTION OF THE DRAWINGS

FIG. 2 is a plan view of a molded orthopaedic wrist brace in accordance with a first preferred embodiment of the present invention;

FIG. 6 is a cross sectional view of the orthopaedic wrist brace taken along line 6—6 of FIG. 2;

FIG. 7 is a sectional view of a portion of an orthopaedic brace in accordance with a second preferred embodiment of the present invention;

FIG. 8 is a perspective view of an orthopaedic wrist brace in accordance with a third preferred embodiment of the present invention in which flexible mesh areas are employed;

FIG. 9 is a perspective view of one preferred structure for securing the straps in place;

FIG. 10 is a perspective view showing an alternative structure for securing the edges of the brace together;

DETAILED DESCRIPTION OF THE PREFERRED EMBODIMENTS

The following is a detailed description of a number of preferred embodiments of the present invention. This description is not to be taken in a limiting sense, but is made merely for the purpose of illustrating the general principles of the invention. The scope of the invention is defined by the appended claims.

Figure 1:
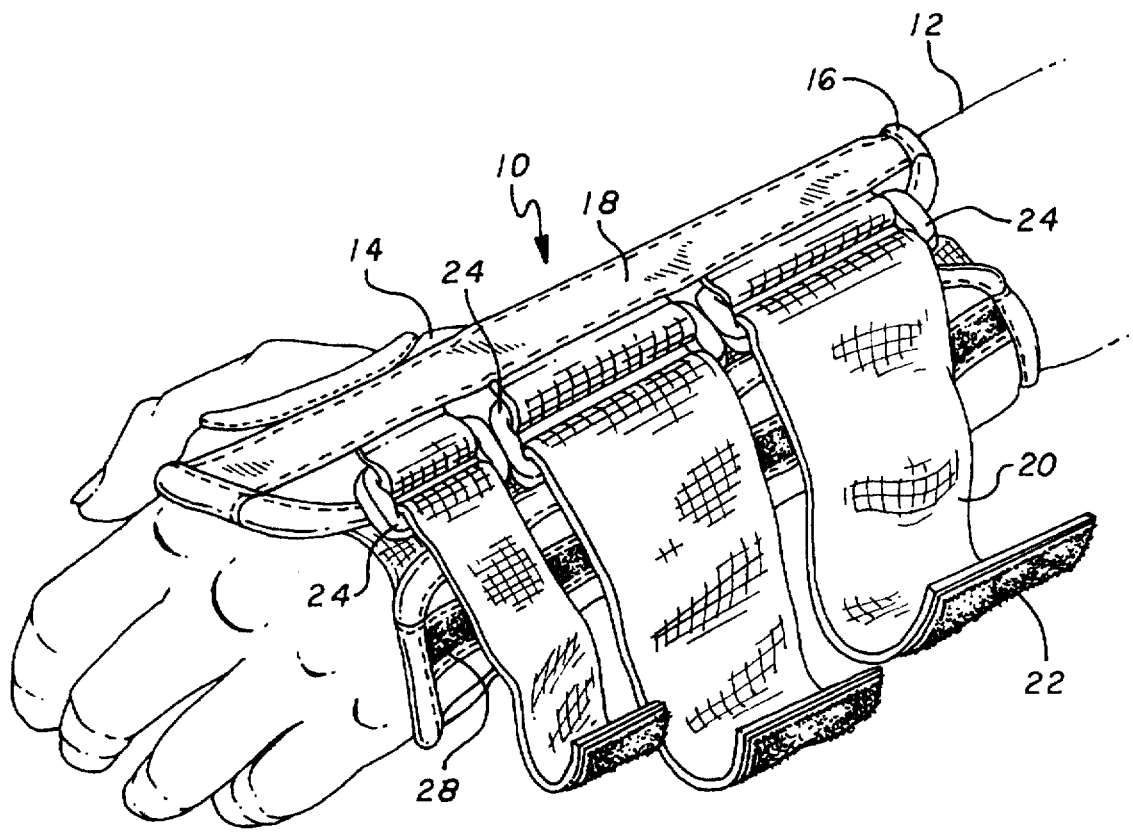
FIG. 1 is a perspective view of a prior art orthopaedic wrist brace.

Referring to FIG. 1, a prior art orthopaedic wrist brace 10 is shown as worn on a left arm 12. The main body 14 of the brace 10 is comprised of numerous discrete pieces of flexible material that are cut to predetermined sizes and shapes and sewn together with stitching 16. In order to stabilize or immobilize the dorsal side (back side) of the injured arm or wrist, an extra piece of material 18 covering, or containing, a rigid splint or stay, is sewn onto the dorsal side of the main body 14. The stay is usually formed of a strip of aluminum or substantially rigid or stiff plastic material. A similar arrangement is usually present on the opposite, volar (or palm), side of the main body 14 to provide extra rigidity (not shown). D-rings 24 are permanently sewn to one edge of the main body 14, while straps 20, carrying a loop material 22, are sewn to the opposed edge of the main body 14. In order to secure the device to the arm 12, the straps 20 are inserted into and through the openings of the D-rings 24 and looped back towards the opposed edge of the main body 14, where the loop material 22 mates with a hook material 28, which is carried by a portion of the main body 14.

Referring to FIG. 2, an orthopaedic wrist brace 40 in accordance with a first preferred embodiment of the present invention is shown. The wrist brace 40 includes a support 42, a support coupling which includes straps 52, 54, 56 and D-rings 62, and padding 64. The support 42 is made of material whose flexibility is a function of its thickness. Examples might include polypropylene, polyethylene, thermoplastics, elastomers, nylon or urethanes, with polypropylene and polyethylene presently being preferred. The support 42 includes thinly molded areas 44 that are relatively flexible and formed so that they conform to the shape of the portion of the hand, wrist and forearm to be supported. In this particular embodiment, the thinly molded areas 44 have eight open areas or holes extending throughout the molded plastic. A thumb hole 46 receives the thumb of the patient and assists in the location and mounting of the wrist brace 40. The remaining open areas are designed to provide extra breathability, and light weight to the wrist brace 40.

Figure 5:
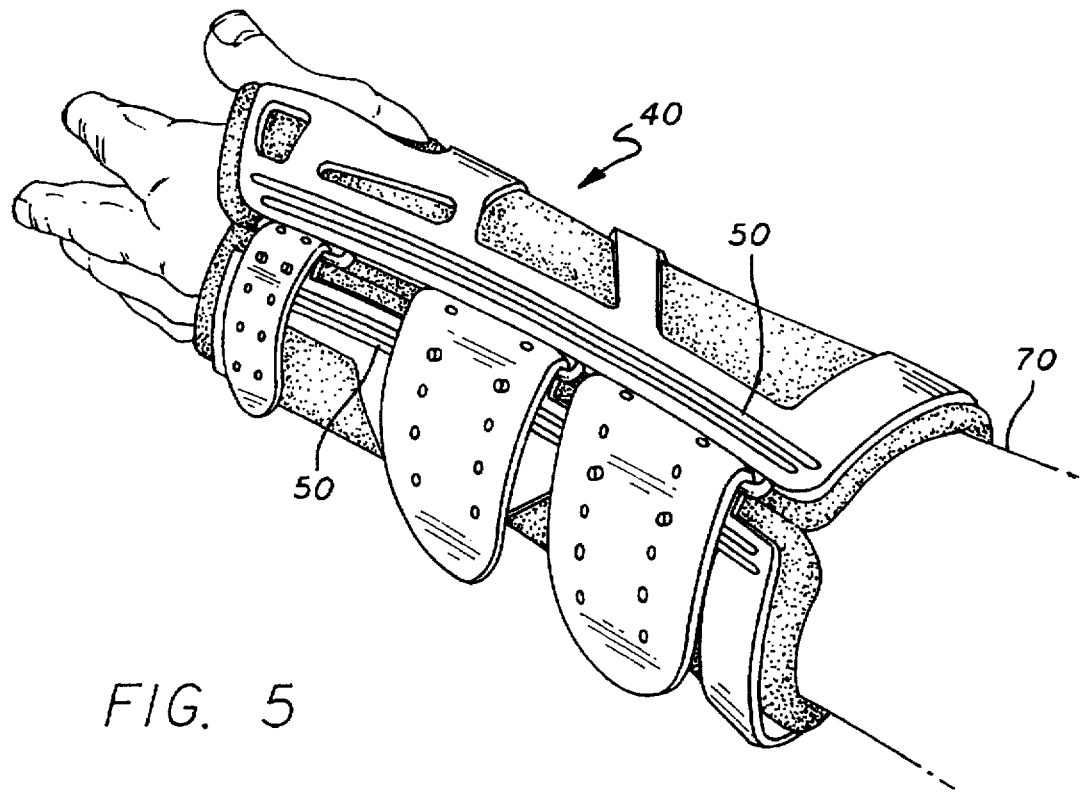
FIG. 5 is a perspective back view of the wrist brace illustrated in FIG. 2 also showing the device secured to the left arm.

A thickly molded area 48 runs longitudinally along the portion of the support 42 that supports the volar side of the hand and arm. This thicker area 48 provides the stiffness needed to achieve desired splinting action and support. The ribs 50 are strips of thicker molded material extending longitudinally along both edges of the support 42 to further provide a desired level of stiffness and to support the dorsal side of the arm, as shown in FIG. 5 and described more fully below. Referring to FIG. 6, the cross-sectional view of the brace 40 reveals the thickly molded area 48 and the ribbed areas 50 in relation to the thinly molded areas 44.

Flexible straps 52, 54 and 56 extend outwardly from the flat edge 60 of the support 42. The D-rings 62 extend outwardly from the edge 61. Each D-ring 62 is sized and located to mate with a corresponding flexible strap 52, 54 or 56. Equally-spaced pairs of small holes 58a and 58b extend longitudinally along a major portion of the strap 52. A pair of pegs 59a and 59b having substantially the same circumference as the holes 58a and 58b protrude at the end of the strap 52 that is adjacent to the support 42. This pair of pegs 59a and 59b mates to any of the pairs of holes 58a and 58b in the manner shown in FIGS. 5 and 9, and have slightly enlarged ends to hold the straps 52, 54 and 56 in place. Straps 54 and 56 have the same hole and peg configuration as strap 52.

An important aspect of this preferred embodiment is that all of the principal elements required to construct a functional brace are produced unitarily; that is, at one time and in one piece. Specifically, the support 42 having the thick area 48, the thin areas 44 and the ribbed areas 50, the straps 52, 54 and 56, and the D-rings 62 are created with a single molding shot. The padding 64 is added to simply provide extra comfort and may not be required.

Figure 3:
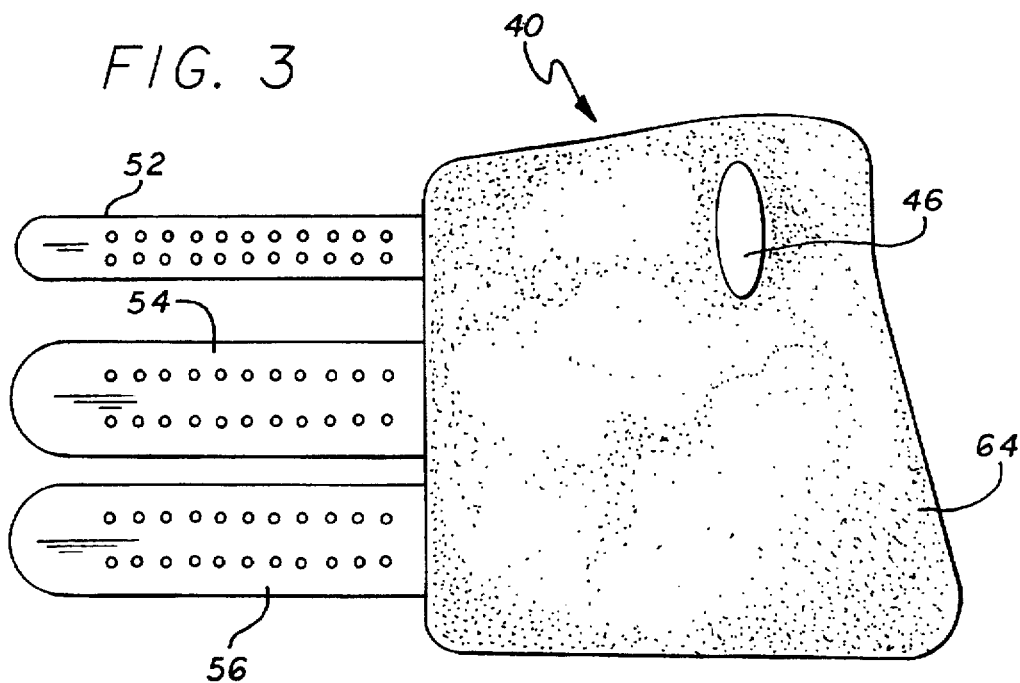
FIG. 3 is view of the padded, inner configuration of the orthopaedic wrist brace illustrated in FIG. 2.

Turning to FIG. 3, the padding 64 of the wrist brace 40 extends over the entire inner side of the support 42, except for the thumb hole area 46. In this way, only the padding 64 directly contacts the patient's arm, providing extra comfort, especially when wearing the wrist brace 40 for long periods of time. The padding 64 may be comprised of a soft, breathable and resilient material, is usually die cut to the desired shape and is secured to the inner side of the support 42 by any of a variety of methods, such as by bonding or by adhesive material.

Figure 4:
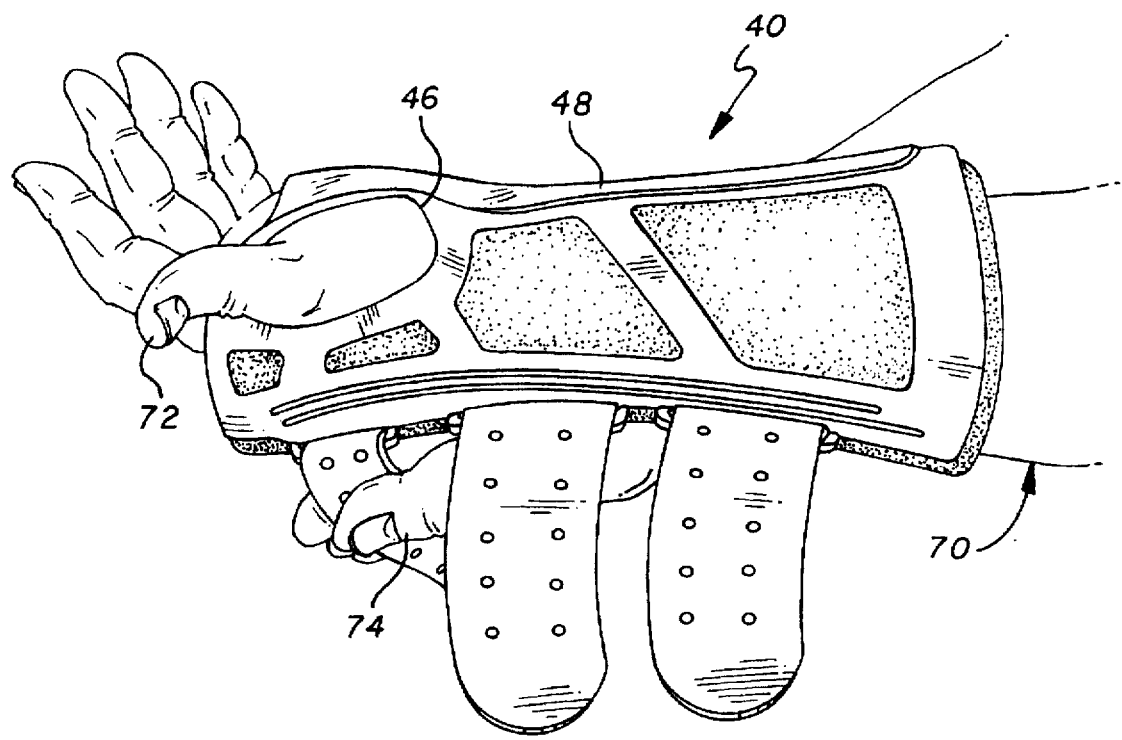
FIG. 4 is a perspective side view of the orthopaedic wrist brace illustrated in FIG. 2 showing the device in the course of being secured to the left arm.

As shown in FIG. 4, the wrist brace 40, when securing to the wrist and arm 70, flexibly conforms to the shape of the wrist and arm 70. The thumb hole 46 receives the thumb 72 and the patient's free hand 74 can easily and firmly secure the wrist brace 40 to the wrist and arm 70, as described in more detail below. The thickly molded area 48 covers a substantial portion of the volar region of the hand, wrist and arm 70, and, due to its thickness, is stiff enough to provide the support and splinting action necessary to prevent the wrist from flexing.

FIG. 5 shows the dorsal side of the patient's arm 70 while wearing the wrist brace 40. When the arm 70 is encased by the wrist brace 40, the two sets of ribs 50 extend longitudinally along the portion of the wrist brace 40 that covers the dorsal region of the hand, wrist and forearm of the arm 70 and provide a desired amount of stiffness to this side of the wrist brace 40. In this way, the dorsal side of the arm 70 and wrist is supported and restrained against flexing.

FIG. 7 shows a partial cross-sectional view of an alternative configuration in which resilient material 71 is co-molded to the molded support 76, extending through small openings 78 in the molded support 76. Co-molding is a process by which the flexible resilient material 71 is molded onto the previously molded principal structure 76 of the brace. In this embodiment, the support 76 is molded with relatively large openings 77 and relatively small openings 78. The co-molded material 71, in its fluid state, is injected to bond to support 76 and to extend across the major openings 77 of the support 76. Further, the co-molded material 71 extends through the smaller openings 78 to effectively secure the co-molded material 71 to the support 76. The co-molded resilient material 71 provides cushioning and comfort to the area of the anatomy to be supported and is an alternative to the die cut padding that requires attachment to the support by means of bonding, adhesives or sewing. Co-molded material 71 may also have holes 74 to provide extra breathability and comfort. The resilient co-molded material 71 is comprised of either SANTOPRENE, available from the Advanced Elastomers division of Monsanto or KRATON, available from Shell Plastics, or an equivalent.

Turning now to the preferred embodiment of FIG. 8, an orthopaedic wrist brace 80 is provided with mesh 84 that is unitarily molded with wrist brace 80, in place of the thinly molded areas 44 and open areas 64 described in the first preferred embodiment and as shown in FIG. 2. Having unitarily molded mesh 84 in areas of the wrist brace 40 that do not require stiff and immobilizing support, provides the benefits of breathability, light weight and even greater flexibility than thinly molded solid areas 44. Furthermore, because of the improved breathability and comfort inherent to this embodiment, separate die cut padding or co-molding on the inner side of the wrist brace 80 is not needed, although either may be added if desired.

The securing method of the wrist brace 40 illustrated in FIG. 2 is shown in more detail in FIG. 9. The free end of the strap 52, having holes 58a and 58b and mating pegs 59a and 59b is fed through the opening of the D-ring 62. The strap 52 is then folded back and over the D-ring 62 and in the direction shown, forcing the two edges 60 and 61 of the support 42 towards one another, until the wrist brace 40 firmly encases the arm and wrist. The pair of holes 58a and 58b that most closely aligns with the pegs 59a and 59b in this position is then snapped onto those pegs 59a and 59b, thereby firmly securing the two edges of the brace 40 together and to the forearm and wrist. These steps are repeated for the remaining straps 54 and 56 and D-rings 62 to firmly secure the entire brace 40. This method is similar to the hole and peg system used on adjustably sized baseball caps. The plurality of pairs of holes 59a and 59b on the straps 52, 54 and 56 enables one size molded brace to fit a wide range of arm sizes.

FIG. 10 shows an alternative arrangement for securing the brace. In this embodiment, a plastic tie locking system replaces the strap and D-ring arrangement described above. Arch-shaped members 90 and 92 are molded at support edges 96 and 98, respectively, and are aligned to each other where the opposed edges 96 and 98 meet. The free end of the plastic tie 94 that carries angled teeth on one side is looped through arch-shaped members 90 and 92 and then pulled through an aperture 95 that is at the opposite end of the plastic tie 94 in the direction shown. Attempting to open and remove the brace by either pulling on the plastic tie 94 or by separating the support edges 96 and 98 causes one of the angled teeth on the plastic tie 94 to engage and lock with an inner portion of the aperture 95 in a pawl and ratchet type fashion, preventing removal. Therefore, the wrist brace may be tightened by pulling on the free end of the plastic tie 94 but may not be loosened. The only way to remove the brace is to cut the plastic tie 94. Then, in order to reuse the brace, the doctor or therapist must supply new plastic ties 94. This preferred embodiment provides a number of benefits. First, this securing method is low cost. Further, since plastic ties 94 can only be removed once, it is less likely that the patient will disobey the doctor's order and cut the plastic ties 94 prematurely. Therefore, this embodiment might be preferred by doctors for use on those patients who lack the necessary discipline to continually wear a removable brace.

Figure 11:
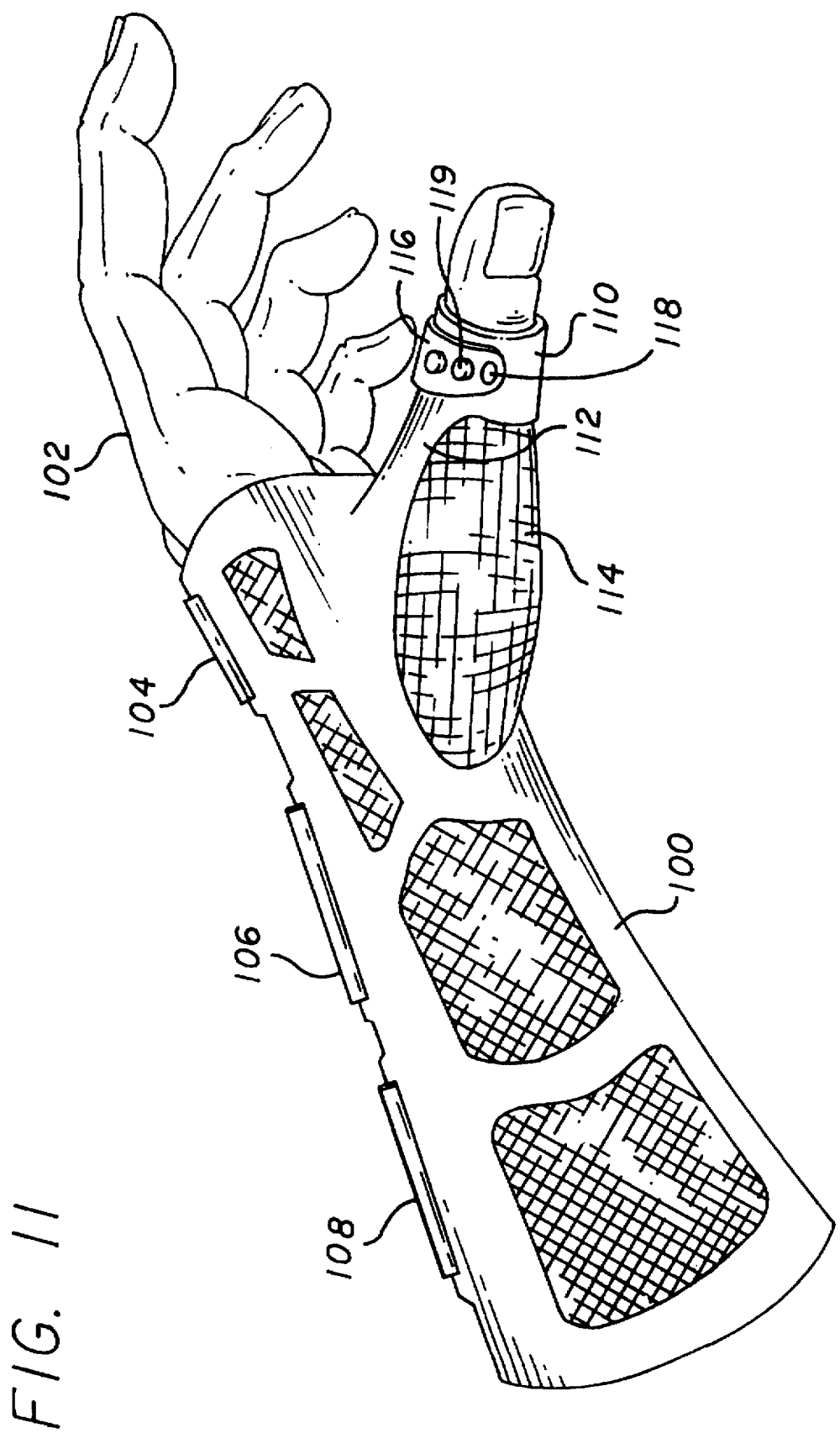
FIG. 11 is a perspective view of an orthopaedic brace in accordance with a fifth preferred embodiment of the present invention in which a thumb support is employed.

FIG. 11 shows a unitarily molded orthopaedic thumb brace or spica 100. The thumb spica 100 is molded with a thumb support 110 to immobilize the thumb of a hand suffering from bone or ligament injury particularly associated with the joint between the thumb and the remainder of the hand and wrist. The thumb support 110 is comprised of a continuous, relatively thick, molded area 112 for support, and mesh area 114 for breathability and light weight. The thickly molded area 112 provides restraint to the thumb support 110. A thumb strap 116 has a plurality of equally sized holes 118, any of which mates to a peg 119 on the thumb support 100. The arm and hand 102 is inserted into the thumb spica 100 and the arm and wrist portion is secured with straps 104, 106 and 108 in the same manner as shown in FIGS. 4 and 9 and as described above. Then, depending on the size of the thumb to be supported, one of the holes 118 on the thumb strap 116 is chosen to snap into the peg 119 so that the thumb support 110 firmly encases the thumb and substantially immobilizes it. As in prior embodiments, the overall structure of thumb spica 100 is unitarily molded.

Figure 12:
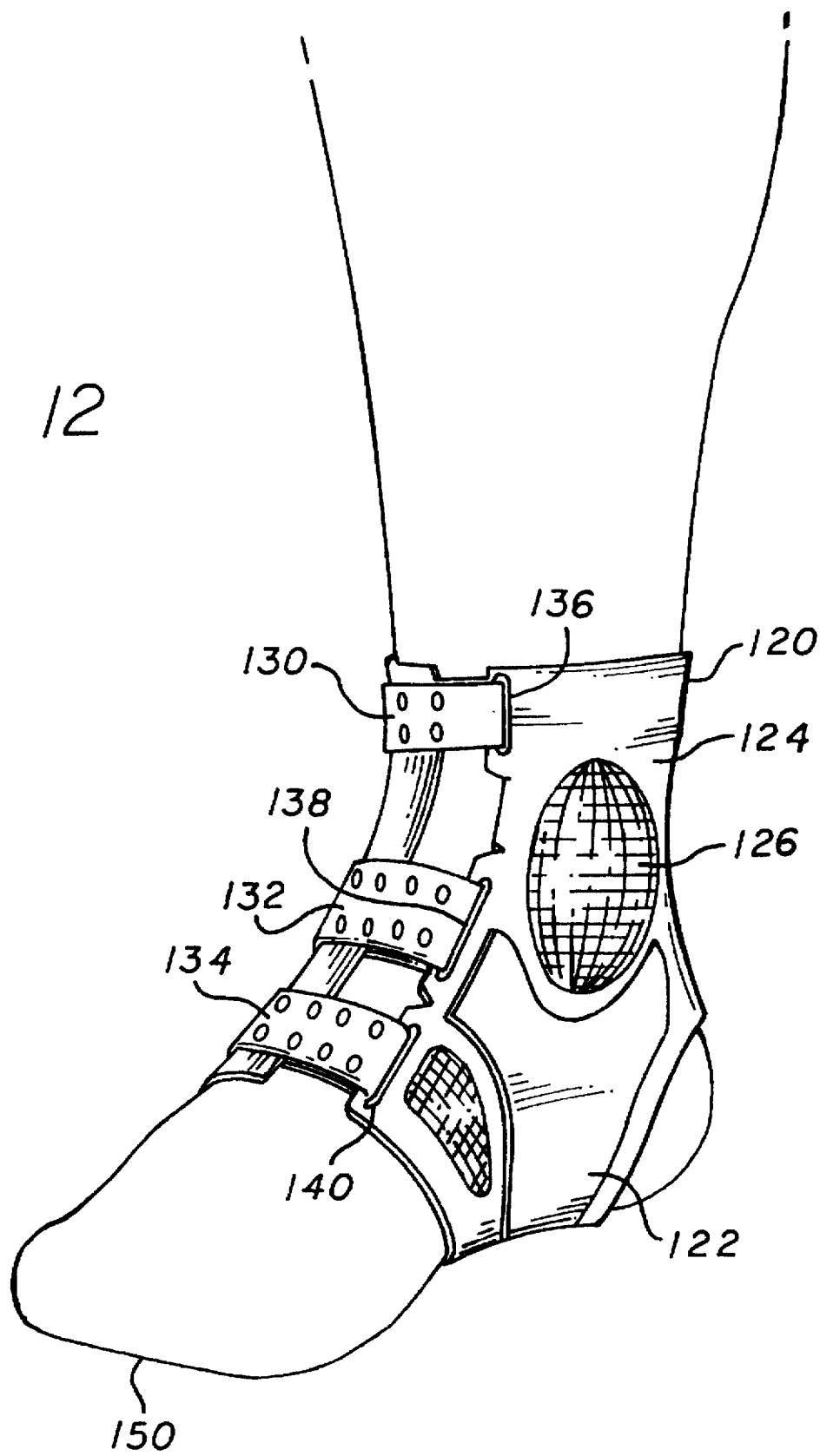
FIG. 12 is a perspective view of a unitarily molded orthopaedic ankle brace.

Referring now to FIG. 12, a unitarily molded ankle brace 120 is shown. The ankle brace 120 has thickly molded areas 122 for providing support to the foot 150, thinly molded areas 124 and mesh areas 126, with the mesh areas 126 being very flexible, to provide comfort to sensitive areas of the foot 150 such as the malleolus or ankle bone. A substantial mirror image of this arrangement is presented on the opposite side of the brace 120 (not shown). The straps 130, 132, and 134, having holes and pegs, work in conjunction with D-rings 136, 138, and 140, respectively, in the manner shown in FIG. 9 and described above, to adjustably secure the mating edges of the ankle brace 120 together at the front of the foot 150. This light weight and low cost ankle brace 120 is useful for protecting and immobilizing the ankle joint in cases of a sprained ankle, a partial ligament tear or the like.

Although the present invention has been described in terms of the preferred embodiments above, numerous modifications and additions to the above-described preferred embodiments would be readily apparent to one skilled in the art.

Thus, by way of example and not limitation, the present invention is not limited to application to wrists, thumbs or ankles. Other unitarily molded orthopaedic braces may be created to support other injured parts of the anatomy such as knees and elbows. Additionally, a variety of features from each of the preferred embodiments may be combined to create new brace configurations. For example, one configuration might be an injection molded support with unitarily molded D-rings, sewn on straps and co-molded padding. Furthermore, the D-rings used in a number of the embodiments described above may be eliminated. In such an alternative embodiment the straps would not have pegs and would not loop back and snap onto itself. Instead, the straps with holes would extend across the opposed edge of the support and would snap into pegs that reside on the opposed side of the support. Also, the number of straps and the number of holes and the orientation of the holes on the straps may vary. In addition, other mechanical arrangements may be provided for securing overlapping edges of the supports together, such as (1) molded hooks or pegs on one edge mating with openings or recesses on the opposing edge, (2) mating hook and loop type areas on the edges, or (3) tensioning ties secured through molded loops on opposing edges of the support.

It is further noted that various components of the support may be integrally injected molded together and other portions added thereto. In addition, portions of the supports as disclosed in the drawings hereof may be molded or otherwise formed of plastic separately and secured together by bonding, snapping or other fastening techniques. Accordingly, it is intended that the scope of the present invention extends to all such modifications and/or additions and that the scope of the present invention is limited solely by the claims set forth below.

What is claimed is:

1. A injection molded orthopaedic support for a part of the anatomy comprising:
    at least one relatively thick area of the support for providing substantially rigid splinting action;
    at least one flexible area of the support that is thin relative to said at least one relatively thick area for adapting the support to conform to and at least partially enclose the part of the anatomy to be supported;
    straps forming part of said support for holding said support in place; and
    said relatively thick area, said relatively thin area and said straps all being integrally injection molded together in a single injection molding step with the same material to form a single unitary support.

2. An orthopaedic support as defined in claim 1 wherein said thinner flexible area includes at least one opening, and an integrally formed mesh that is formed in the same injection molding step as said thicker and thinner areas and that extends across said opening.

3. An orthopaedic support as defined in claim 1 wherein a layer of resilient material is mounted within said support for cushioning the support where it engages the part of the anatomy being supported.

4. An orthopaedic support as defined in claim 3 wherein the resilient material is co-molded securely onto the support.

5. An orthopaedic support as defined in claim 1 wherein said support is a wrist support and wherein at least a portion of said support has been molded to substantially match the contour of a human wrist.

6. An orthopaedic support as defined in claim 1 further comprising a thumb support that has been unitarily molded the same molding step as said thick area and said thin flexible area for supporting and substantially immobilizing a thumb.

7. An orthopaedic support as defined in claim 1 wherein said support is an ankle support.

8. An orthopaedic brace for supporting a selected portion of the anatomy, including:
    a support, being unitarily injection molded and specifically contoured with areas of differing thicknesses formed in a single injection molding step to adapt to the contour of the selected portion of the anatomy, the support having opposed edges, the support also having substantially flexible areas for extending around and engaging the selected portion of the anatomy, and having substantially rigid portions having a thickness substantially greater than the flexible areas of the support for providing rigidity and splinting or support function, said flexible and said substantially rigid portions being formed from the same material; and
    a support coupling that has been unitarily injection molded together with and at the same time as the support and that is located at the opposed edges of the support for holding the opposed edges toward one another and for adjustably and removably securing the support onto the selected portion of the anatomy.

9. An orthopaedic brace as defined in claim 8 wherein the flexible areas include openings that are formed in the same injection molding step as support.

10. An orthopaedic brace as defined in claim 9 wherein at least some of said openings are covered with a mesh that is unitarily molded at the same time as the support.

11. An orthopaedic brace as defined in claim 9 wherein a layer of flexible material is co-molded onto an inner surface of the support.

12. An orthopaedic brace as defined in claim 8 wherein the support has an inner surface and a shape, and a cushioning material substantially conforming to the shape of the support is removably secured to the inner surface of the support.

13. An orthopaedic brace as defined in claim 8 wherein the support coupling is comprised of at least one strap located at a first edge of the support, the support coupling having at least one hole in each of the straps and at least one mating peg, the entire support, including said strap, the hole and said peg, being formed in a single molding step.

14. An orthopaedic brace as defined in claim 13 wherein a second edge of the support opposed to the first edge of the support comprises at least one unitarily molded D-ring corresponding to each strap for looping the strap therethrough, said support, including said D-ring, being integrated together in the same molding step.

15. An orthopaedic brace as defined in claim 8 wherein the securing means is comprised of at least one removable plastic locking type tie.

16. An orthopaedic brace as defined in claim 8 wherein support is a wrist support.

17. An orthopaedic brace as defined in claim 8 wherein said support is a thumb support.

18. An orthopaedic brace as defined in claim 8 further comprising a thumb support unitarily molded with the support and having substantially thick portions, substantially flexible areas that are thin relative to said thick portions, and an adjustable thumb receiving opening.

19. An orthopaedic brace as defined in claim 8 wherein said support is an ankle support that has been molded to mate with the contour of an ankle.

20. An orthopaedic brace for a wrist including:
    a support, being unitarily molded and preformed to conform to the shape of a portion of the arm encompassing and including the wrist, the support having opposed edges, substantially flexible areas for extending around and engaging the wrist, and have substantially rigid portions for extending longitudinally along the volar and dorsal planes of the arm and having a thickness substantially greater than the flexible areas of the support for providing rigidity and splinting or support function, said support being molded from a single material; and
    a support coupling that is molded unitarily and substantially simultaneously with the support, and located at one edge of the support for holding the opposed edges toward one another and for adjustably and removably securing the support onto the portion of the arm encompassing and including the wrist;
    wherein said support and said support coupling are formed by injection molding.

21. A molded orthopaedic support for a part of the anatomy comprising:

a molded support body having at least one relatively thick, substantially rigid area for providing substantially rigid splinting action and at least one flexible area that is thin relative to said relatively thick area for conforming to and at least partially enclosing the part of the anatomy to be supported;

securing means forming part of said support for holding said support in place; and said thicker area and said thinner areas both being integrally molded together the same injection molding step to form a single unitary support.

22. An injection molded orthopaedic support for a part of the anatomy comprising:

an injection molded support body having a contour that generally conforms to a portion of the human anatomy to be supported;

said support body having flexible areas that are thinner than other areas of the support said flexible areas serving to adapt said support to conform to and to at least partially enclose the part of the anatomy to be supported, said support body being formed of a single material;

securing means forming part of said support body for holding said support in place; and said support body and said securing means being integrally molded together in a single injection molding step to form a single unitary support.

23. A molded orthopaedic support as deemed in claim 22, wherein said support body further comprises at least one substantially rigid portion for providing splinting to the part of the anatomy.

24. A molded orthopaedic support as defined in claim 23 wherein said substantially rigid portion is integrally molded with said flexible areas and said securing means in a single injection molding step.

25. A molded orthopaedic support for a part of the anatomy comprising:

a support body having a relatively thick, substantially rigid injection molded area for providing substantially rigid splinting action;

said support body further comprising flexible areas that are relatively thinner than said relatively thick areas for adapting said support to conform to and to at least partially enclose the part of the anatomy to be supported;

said relatively thick, substantially rigid area and said flexible, relatively thin areas being molded of plastic in a single molding step and secured together to form an orthopaedic support; and said support including straps for holding said support in place; said support body and said straps being injection molded from the same material.

26. A molded orthopaedic support for a part of the anatomy comprising:

a support body having a first injection molded, substantially rigid area of the support for providing substantially rigid splinting action;

said support body having flexible injection molded areas of the support for conforming to and at last partially enclosing the part of the anatomy to be supported;

said substantially rigid area and said flexible areas being injection molded together of the same plastic to form an orthopaedic support;

securing means for holding said support body in place; and said support including a layer of cushioning material interfaced between the support body and the portion of the anatomy being supported.

* * * * *